United States Patent [19]

Copelin et al.

[11] 4,197,248

[45] Apr. 8, 1980

[54] REDUCTION IN CHEMICAL OXYGEN DEMAND OF WATER FROM CRUDE TETRAHYDROFURAN

[75] Inventors: Harry B. Copelin, Wilmington, Del.; Thomas D. Canby, West Chester, Pa.

[73] Assignee: E. I. Du Pont de Nemours and Company, Wilmington, Del.

[21] Appl. No.: 889,039

[22] Filed: Mar. 22, 1978

[51] Int. Cl.² .................. B01D 3/34; C07D 307/08
[52] U.S. Cl. ..................... 260/346.11; 203/14; 203/37; 203/42
[58] Field of Search ............ 260/346.11; 203/37, 203/42, 39, 14, 10, 43–46

[56] References Cited

U.S. PATENT DOCUMENTS

| | | | |
|---|---|---|---|
| 1,466,435 | 8/1923 | Hammond | 203/37 |
| 2,251,835 | 4/1941 | Reppe et al. | 260/346.11 |
| 2,366,464 | 1/1945 | Wilson | 260/346.11 |
| 2,485,329 | 10/1949 | Steele | 203/37 |
| 2,779,721 | 1/1957 | Houtmann et al. | 203/37 |
| 3,138,545 | 6/1964 | Reed et al. | 203/14 |
| 3,410,760 | 11/1968 | Craig et al. | 260/346.11 |
| 3,694,465 | 9/1972 | Kisaki et al. | 203/37 |
| 3,726,905 | 4/1973 | Coates et al. | 260/346.11 |

OTHER PUBLICATIONS

*Equilibrium in the Systems of Tetrahydrofuran–Water–Alkali Metal Salts*: Kisaki et al., 1972, Translation.

*Primary Examiner*—Wilbur L. Bascomb, Jr.

[57] ABSTRACT

A process for reducing the chemical oxygen demand of water removed from a mixture of crude tetrahydrofuran and water, said process comprising contacting said mixture in the vapor phase with a dilute sodium hydroxide solution, then optionally contacting the tetrahydrofuran-water mixture after condensation with a concentrated sodium hydroxide solution and separating water from the thus treated mixture, said water having reduced chemical oxygen demand over water that is removed from said mixture merely by distillation.

6 Claims, 2 Drawing Figures

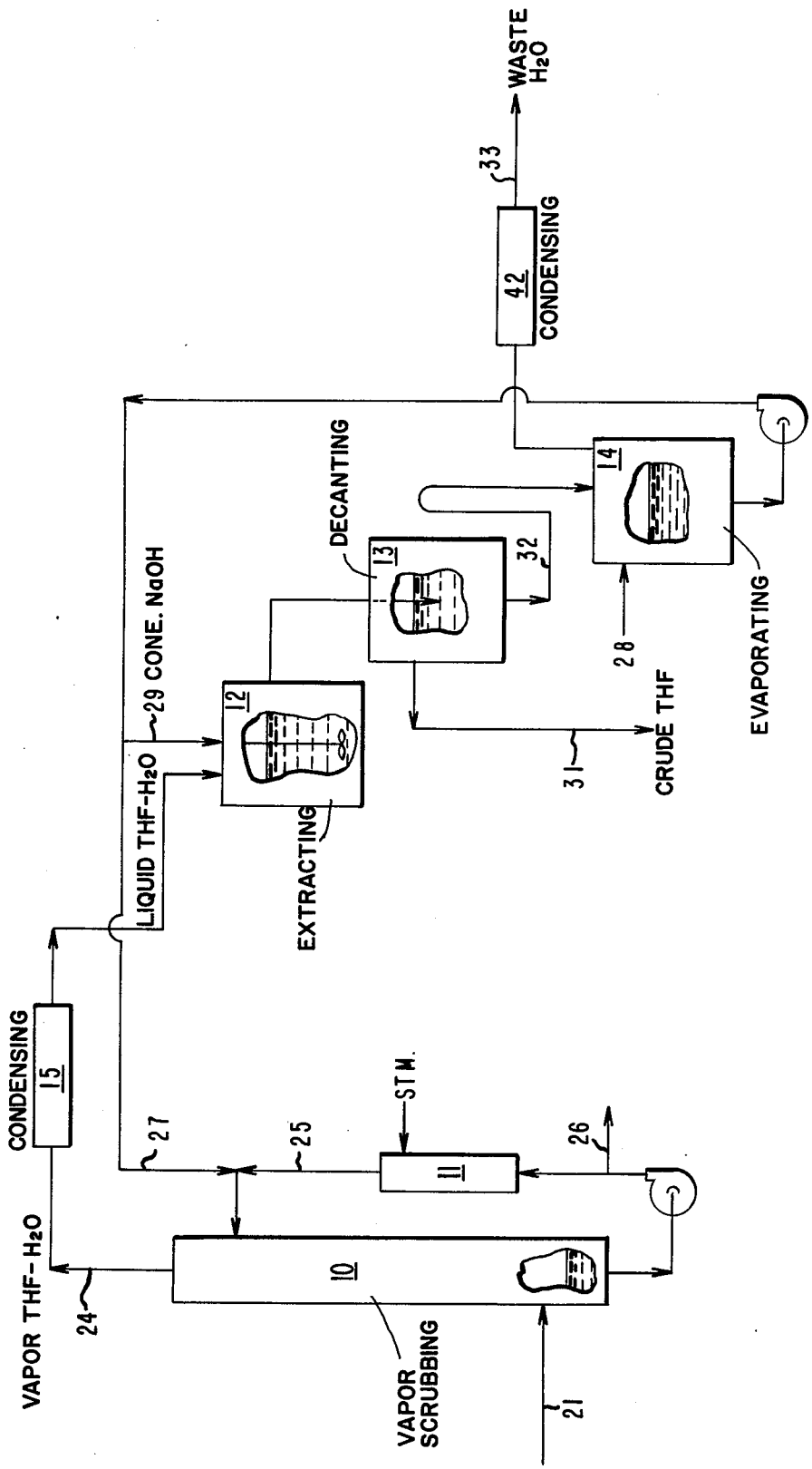

REDUCTION IN CHEMICAL OXYGEN DEMAND OF WATER FROM CRUDE TETRAHYDROFURAN

DESCRIPTION

Technical Field

This invention relates to a process for minimizing the chemical oxygen demand of water separated from a crude tetrahydrofuran-water mixture. More specifically, this invention relates to a process for minimizing the chemical oxygen demand of water that is separated from a crude tetrahydrofuran-water mixture by contacting the mixture in the vapor phase with a dilute sodium hydroxide solution.

Background Art

Processes for the cyclization of 1,4-butanediol to form tetrahydrofuran are known in the art. Crude THF-water mixtures resulting from the cyclization of 1,4-butanediol possess unknown impurities which result in high chemical oxygen demand (COD) of waste water derived therefrom. Waste water derived from THF-water mixtures by distillation alone contain COD at levels above that permitted for discharging into waterways by governmental agencies. Water pollution restrictions have made it mandatory that the COD of said water be reduced to certain allowable limits before discharging said water into streams or waterways. Treatment of this waste water with absorbents such as active charcoal is very costly and of limited effectiveness. Incineration of said waste water is impractical due to the large quantity of water involved.

DISCLOSURE OF INVENTION

Now it has been found that the reduction of COD in the water removed from a crude THF-water mixture is 50 to 70% of that present in the water that was removed by mere distillation when a process is used which comprises contacting said crude THF-water mixture in the vapor phase with a 5 to 35% by weight solution of sodium hydroxide, subjecting the vapors of the crude THF-water mixture to distillation and removing water from said mixture with the reduced COD. The contacting of the aforesaid caustic solution and THF-water mixture is under conditions that permit the recovery of the mixture in vapor form and the maintenance of the concentration of the caustic solution within the range described.

In the production of THF from crude 1,4-butanediol by cyclizing said diol in the presence of an acid, e.g., sulfuric acid, a mixture of crude THF and water results with impurities having high levels of chemical oxygen demand (COD). This THF-water mixture with said impurities can be purified by distilling or fractionating said mixture into a THF-water azeotrope and excess water with high COD.

Accordingly, in the process of cyclizing 1,4-butanediol to form a crude mixture of THF and water followed by the purification of said mixture by distillation to yield a THF-water azeotrope and waste water with high COD, the present invention is the improvement wherein the crude THF-water mixture, before distillation, is contacted in the vapor form with a solution of sodium hydroxide at a concentration of from 5 to 35% by weight sodium hydroxide and then subjected to distillation whereby water is removed with a reduction in said COD of from 50 to 70%.

A further embodiment of the present invention involves the substitution, in place of the distillation that follows the dilute sodium hydroxide treatment of the aforesaid process, of a concentrated sodium hydroxide treatment that results in a reduction in the COD in the waste water of up to 90%, preferably 99.5% of the COD present in the waste water separated by distillation alone. When the vapor mixture scrubbing with dilute sodium hydroxide is coupled with a scrubbing of the THF-water mixture in liquid form with concentrated sodium hydroxide, not only is the aforesaid reduction of COD in the waste water achieved, but also the formation of insoluble compounds, that makes the separation of THF and sodium hydroxide solution more difficult or impossible, is minimized.

Chemical oxygen demand (COD) as used herein means the presence of relatively very small amounts of various organic impurities (byproducts) formed in the preparation of 1,4-butanediol or its cyclization to THF. The determination of COD in water is by methods known in the art and is described in *Standard Methods for the Examination of Water and Waste Water*, 13th Edition 1971, APHA, AWWA, WPCF, pp. 495 to 498. All COD determinations in this specification involve water samples. Obviously the COD of these organic byproducts cannot be determined from a sample containing THF. Thus, in the present application, all comparisons of COD are based on the COD in water that was separated by the present invention as compared to that separated by mere distillation.

After the treatment of the THF-water mixture in vapor form with dilute sodium hydroxide solution, the THF-water in vapor form may be condensed and is subjected to distillation or fractionation for water removal. The water removed by this distillation is waste water and contains the reduced amount of COD based on the COD that results when distillation alone is used.

The dilute caustic is continuously recirculated within a closed system and contacts the vapor of the THF-water mixture in a scrubber or a mixing tank, thereby increasing the concentration of the COD due to said impurities in the caustic solution while reducing it in the crude starting mixture. Some of the COD due to byproduct impurities that is present in the crude THF-water mixture is removed with the dilute caustic. The remaining COD due to said impurities is removed with the water via distillation. Contact time of vapors and dilute caustic is generally from 0.1 to 100 seconds, preferably 1 to 10 seconds to give adequate scrubbing.

The COD due to the impurities accumulates in the dilute caustic until an undesirable level is reached at which time an amount is removed for the purpose of neutralizing residues from the cyclization of BAD, said residues comprise sulfuric acid, tars and high boilers. These residues are then incinerated. Generally said residues are continuously removed from the cyclization reactor for purposes of incineration, but they may be removed periodically. The aforesaid dilute caustic for neutralization likewise may be added continuously or periodically. This removal of dilute sodium hydroxide sufficiently reduced the COD of the dilute caustic to permit continued operations.

The dilute caustic of this invention is from 5 to 35% by weight sodium hydroxide in water, preferably 15 to 25% by weight. Lower concentrations are operable but cause the incineration of the high boilers and tars to require more energy due to increased amounts of water being present in the neutralization material. Higher concentrations are also operable but result in corrosion problems.

The temperature and pressure at which the dilute caustic contacts the THF-water mixture varies rather widely. Any temperature and pressure may be used that will permit the vapors of THF-water to be removed as a vapor after contact with the caustic while maintaining the concentration of the sodium hydroxide within the aforesaid concentration range of 5 to 35% by weight. If the temperature is too high, the sodium hydroxide solution will be concentrated while if the temperature is too low, the sodium hydroxide solution will be diluted. Generally a temperature of from 0° to 100° C. is used. The pressure, of course, is dependent on the temperature. If one first establishes a pressure, the temperature must be such that the concentration of the dilute caustic is maintained within the 5 to 30% concentration. Generally, a pressure of from 0 to 100 psig is used. However, pressures below atmospheric and above 100 psig may be used without advantage. The preferred pressure range for the process of this invention is 0 to 20 psig. For example, at 90° C. and atmospheric pressure, the process of this invention was operated with 20.9% NaOH.

The reduction in the COD of the waste water obtained from the THF-water mixture after scrubbing with dilute caustic and distillation or fractionation was 50 to 70% of the COD in the waste water obtained by merely distilling the THF-water mixture. The reduction in COD is achieved by the dilute caustic which picks up some of the impurities that give the COD.

The concentrated caustic contact with the THF-water mixture in liquid form may be in a mixing vessel with agitation means or in a scrubber tower. Contact time may vary rather widely depending on the conditions and the mixture composition.

The concentrated caustic of this invention is generally from 35 to 55% by weight sodium hydroxide in water, preferably 45 to 50% by weight. More dilute caustic will not extract as much water while more concentrated caustic requires excessive temperature in the subsequent concentration unless reduced pressures are used. Corrosion is also more of a problem at higher concentrations.

The THF-water mixture, after treatment with the concentrated caustic, is allowed to settle to permit separation of the THF phase from the aqueous sodium hydroxide solution phase. The vapor treatment with dilute sodium hydroxide solution permits this phase separation to be made with minimum difficulty. When the THF-water mixture in the vapor form is not first scrubbed with dilute sodium hydroxide, this separation is complicated by the presence of insoluble compounds that build up at the interface. These insoluble compounds which result when the THF-water mixture is treated only with concentrated sodium hydroxide build up and make the separation more difficult or impossible. When both the dilute sodium hydroxide treatment and the concentrated sodium hydroxide treatment are involved, the presence of the insoluble compounds is minimized.

After the scrubbing of the liquid THF-water mixture with the concentrated sodium hydroxide solution and separation of the caustic solution from the THF, sufficient water is removed from the concentrated caustic solution to maintain the concentration of the concentrated caustic solution in the range required for the scrubbing. During the scrubbing of the THF-water mixture, the concentrated caustic solution picks up water. For example, 50% sodium hydroxide may be diluted to the range of 35 to 40% sodium hydroxide. This diluted sodium hydroxide is then concentrated to the concentration desired. This water removed is discharged and constitutes waste water.

The temperature and pressure at which the concentrated caustic scrubbing is conducted may vary widely. Any temperature and pressure that will not result in the concentration of the caustic solution beyond the range of 35 to 55% by weight, preferably 40 to 50%, and that will not vaporize the THF-water mixture may be used. Generally, temperatures of from 20° to 70° C. and preferably temperatures of from 50° to 55° C. at atmospheric pressure are used. Lower temperatures are less efficient because of the temperature differential between the scrubber and the caustic concentrator. Although higher temperatures are operable, they require above atmospheric pressure to prevent loss of THF and offer no advantage.

Surprisingly, it was found that the dilute sodium hydroxide treatment removes COD due to impurities or byproducts from the THF-water mixture, while the concentrated sodium hydroxide treatement drives the COD due to impurities into the THF-water azeotrope. This results in a waste water with substantially less COD that can be discharged into waterways without violation of environmental regulations.

BRIEF DESCRIPTION OF THE DRAWINGS

FIG. 2 is a flow drawing illustrating the process of the invention when both dilute caustic treatment and concentrated caustic treatment of a THF-water mixture are used.

Referring now to FIG. 1, crude 1,4-butanediol (BAD) and sulfuric acid enter cyclization reactor 1. Crude THF and water in vapor form leave the cyclization reactor and pass through reactor column 2 where unconverted BAD is condensed and returned to the reactor. The crude THF-water vapors pass through a partial condenser 5 and enters dilute caustic scrubber 6. The temperature of the recirculating dilute caustic from surge tank 7 is maintained by heater 8 so that the water content of the THF-water mixture shows negligible change during the scrubbing operation. This temperature range depends on the caustic concentration and the pressure in the dilute caustic scrubber 6. At atmospheric pressure and 20% by weight caustic, this temperature and the temperature in the scrubber 6 should be about 90° C. Scrubber 6 consists of a tower which may be packed with Raschig rings or other packing or have trays that are normally used for distillation such as bubble cap, shower, valve, etc. The scrubber can be operated with continuous liquid phase (flooded) or continuous vapor phase in which liquid flows down the column. The tower design should allow a vapor contact time of 0.1 to 100 seconds with a preferred contact time of 1 to 10 seconds. Inadequate scrubbing reduces the efficiency, thereby allowing impurities to pass through the scrubber which can interfere with decanting operations necessary when further treatment of the THF-water mixture is involved. Excessively long contact time is not harmful but requires larger and more expensive equipment. Scrubbed THF-water vapor is then passed to distillation column 9 where a THF-water azeotrope of about 6% water is separated via the top from excess water. The excess water leaves column 9 from the bottom and is waste water with reduced COD. The THF-water azeotrope leaving the top of column 9 is then further purified. The bottoms from the cyclization reactor 1 pass to an evaporator 3 from where some material is recycled back to the reaction. The bottoms are neutralized in 4 with dilute caustic from 6 and then are taken to incineration.

Figure 1:
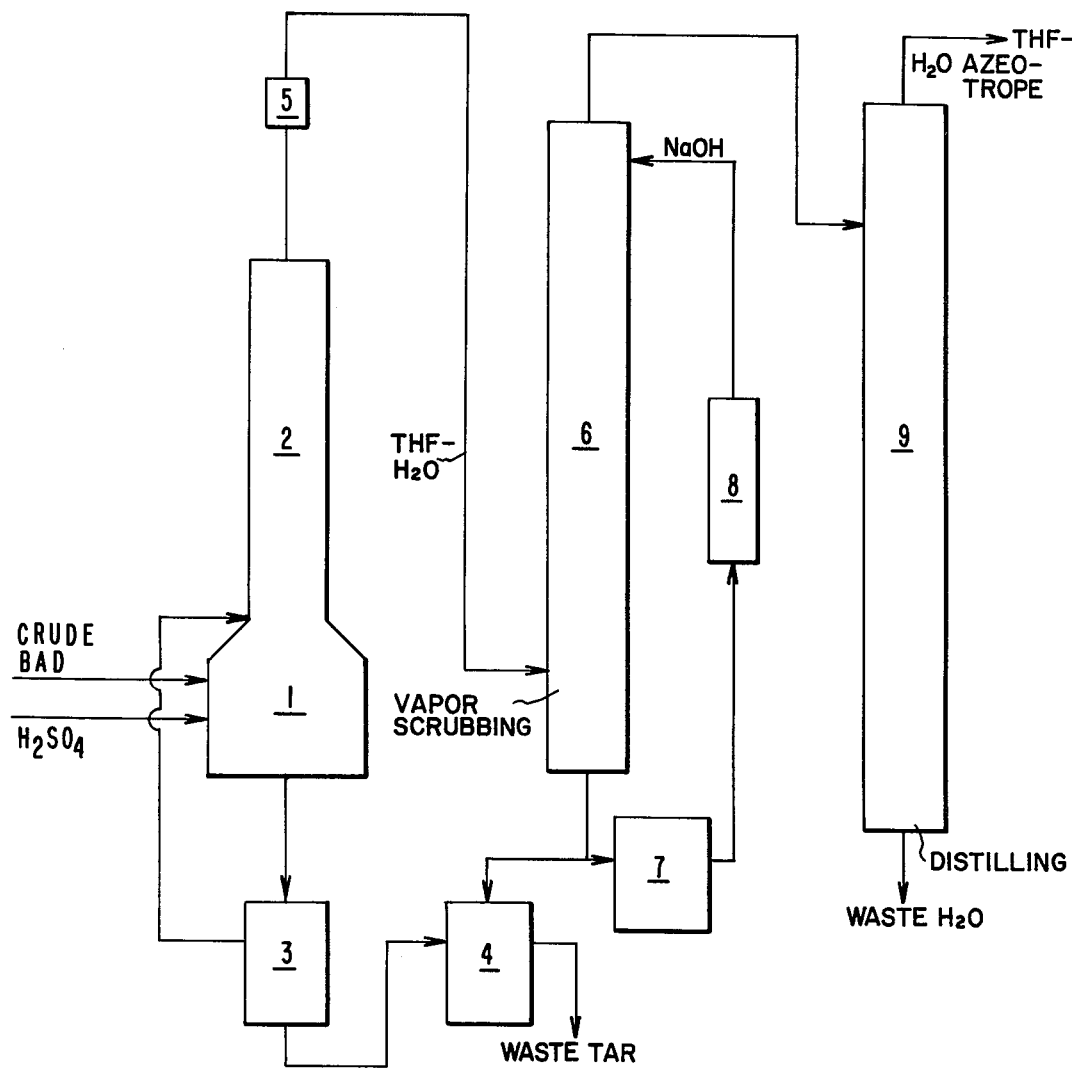
FIG. 1 is a flow drawing illustrating the process of the invention when only the dilute caustic treatment is used.

Referring now to FIG. 2, crude THF-water 21 vapor from a BAD cyclization reactor enters dilute scrubber 10 in vapor form. Dilute caustic solution is collected in the bottom of the scrubber and pumped through heater 11 via 25 back to the top of the scrubber. Scrubbed THF-water vapors 24 leave the scrubber and pass through a condenser 15 and the condensed mixture enters mixing vessel 12 where it is intimately contacted by mixing with concentrated caustic which enters via 29. The resulting mixture of caustic-water-THF overflows vessel 12 and enters decanter 13 where it immediately forms two layers. The bottom layer caustic solution is drained via 32 to a caustic concentrator 14 which evaporates the excess water picked up by the caustic. Fresh caustic makeup can be added via 28. Water removed for concentrator 14 is condensed in condenser 42 and the water condensed is waste water 33 with reduced COD. In a commercial facility this water would be discharged into a biopond prior to being discharged into an existing waterway. The upper layer from the decanter 13 which is an extracted azeotrope THF-water leaves the decanter via 31 for further purification. Concentrated caustic can be fed via 27 if necessary to the dilute caustic. Caustic removal to lower the COD content of the dilute caustic and to neutralize bottoms from the cyclization reactor to be incinerated is made via 26.

When the concentrated caustic is about 50% by weight caustic, the THF from the decanter at 31 will contain about 0.5 to 1.5% water and essentially all of the organic impurities normally present in the crude THF.

Mix vessel 12 may also be a packed or plate type tower, but a mix vessel is preferred.

The presence of undesirable impurities in the form of insoluble compounds, which tend to build up causing plugging and difficulties in separation in the decanter or in an extractor tower if used in place of the mix tank and decanter, is minimized by the combined dilute caustic and concentrated caustic scrubbing.

The dilute caustic treatment of vapors of crude THF-water extracts COD due to impurities with the dilute caustic, while concentrated caustic treatment of the crude THF-water leaves said COD in the THF. The presence of COD due to impurities in the THF presents no problems. The use of only a concentrated caustic scrubber to achieve a reduction of COD in waste water results in excessive amounts of insoluble compounds in the decanter for separation, thereby making separation difficult or impossible.

Under some operating conditions, the presence of a fine suspension of THF is present in the concentrated caustic stream from the decanter. This THF can be removed with the water that is removed by concentration of the caustic and since THF is biodegradable, its presence in waste water is not a problem.

BEST MODE

The process of the invention is further illustrated by the examples that follow wherein all percentages are by weight unless otherwise indicated. The examples reflect the best mode of the process of the invention.

In the examples, crude THF-water vapors were fed to a scrubber column. Dilute caustic was pumped to the top of the column through a heater. The scrubber column was a 1.5" I.D. glass tube packed 18" deep with 0.25"×0.25" pieces of glass tubing with a bottom section or pot of 500 cc. The system was heated and insulated to avoid heat loss. The dilute caustic recirculation loop was fitted with connections for caustic purge and makeup. The scrubbed vapors were condensed, then allowed to flow into a one-liter stirred flask where it was contacted with concentrated caustic. The resulting dispersion overflowed through a line to a one-liter decanter. From the decanter, the upper layer (~1% H₂O in THF) overflows into a receiver. The lower layer is drained into a 2-liter flask (operating level 1-liter) which also serves as a concentrator. Water that was removed by concentration of the lower caustic layer was collected and analyzed. The caustic, concentrated to starting concentrations, was cooled to 50° and returned to the mix vessel. Periodically a purge was taken from the weak caustic loop and a corresponding amount of new strong caustic was added.

EXAMPLE 1

Crude 1,4-butanediol from a commercial facility was fed to a cyclization reactor consisting of a pot with a 10 plate 2 inch Oldershaw column with sulfuric acid and tall oil and the crude THF-water mixture exiting overhead was subjected to distillation whereby water and an azeotrope of THF-6% water were separated. An average of the COD test results of the separated water was 37,996 mg/liter.

The crude THF-water mixture was then subjected to dilute caustic scrubbing followed by scrubbing with concentrated sodium hydroxide as described in FIG. 2. The THF-water mixture was not subjected to distillation. After 36 hours the steady-state reduction in COD of the water was 96%. The COD of the water removed from the concentrated caustic was 1500 mg/liter.

The concentrated caustic (50% NaOH) extraction was then stopped and the crude THF-water mixture was subjected to scrubbing with dilute caustic (20% NaOH) as described above and in FIG. 1 and then distilled to remove excess water. After 85 hours, the average COD value in the water was 17,580 mg/liter, a reduction of 54% in the COD.

EXAMPLE 2

Crude THF-water (73.7% THF) from a commercial BAD cyclization facility was fed to the system according to the procedure described above and in FIG. 2 at 9.6 gr/min for a period of 38 hours. The dilute caustic was 20.9% NaOH, the concentrated caustic was 50% NaOH, the temperature in the dilute scrubber was 90° C., the temperature in the concentrated caustic mixing tank was 50° C. The average COD of the water from the concentrated caustic that was extracted from the THF-water mixture was 309 mg/liter. The average COD in the water separated after the crude THF-water mixture was subjected to dilute caustic treatment followed by distillation was 8621 mg/liter of water.

The crude THF-water was then fed directly to a distillation column, bypassing both the dilute and concentrated caustic scrubbing and the water separated in the distillation column was tested for COD. The COD in this water was 20,082 mg/liter. Thus, the reduction in COD by vapor scrubbing with dilute caustic was 57% and the reduction in COD by both dilute caustic and concentrated caustic treatment was 99%.

EXAMPLE 3

The procedure of Example 2 was repeated for a period of 86 hours. The average COD in the water separated merely by distillation was 31,009 mg/liter, the average COD in the water separated by dilute caustic treatment followed by distillation was 8558 mg/liter and the average COD in the water extracted by the concentrated caustic after dilute caustic treatment was 2956 mg/liter. Thus, the reduction in the COD in the water after vapor scrubbing with dilute caustic followed by separation by distillation was 72% and 91% after treatment with dilute caustic and concentrated caustic without distillation.

Some THF is usually present in the water from the concentrated caustic. Since THF is biodegradable, it was not considered a pollutant and therefore not removed. Removal of the THF from the water from the concentrated caustic increased the reduction in COD in this example to 99%.

EXAMPLE 4

Crude THF-water from a commercial BAD cyclization facility is fed to a concentrated caustic scrubber and water extracted as described above for a period of 12 hours. The concentrated caustic was between 35 and 55% by weight sodium hydroxide in water. The COD of the extracted water is about 5% of the COD of the water separated by diverting the feed around the concentrated caustic scrubber to a distillation column. The decanter used to separate the concentrated caustic and the THF after about 5 hours begins to discharge increasing amounts of THF with the concentrated caustic and increasing amounts of caustic with the THF. The decanter is inspected and is found to contain insoluble compounds which interfere with the separation of the two phases.

INDUSTRIAL APPLICABILITY

The present process makes it possible to meet water pollution restrictions of nonbiodegradable COD imposed by governmental agencies on plant effluent from THF purification facilities. Additionally, the process involving both dilute caustic and concentrated caustic scrubbing removes the necessity of a distillation column for removal of water thus saving energy. The process finds applicability in processes involving the preparation of THF from BAD.

While the invention has been described in considerable detail in the foregoing, it is to be understood that such detail is solely for the purpose of illustration and that variations can be made by those skilled in the art without departing from the spirit and scope of the invention except as set forth in the claims.

We claim:

1. In the process of cyclizing 1,4-butanediol to form a mixture of crude tetrahydrofuran and water followed by the purification of said mixture by distillation to yield a tetrahydrofuran-water azeotrope and waste water, said waste water having a high chemical oxygen demand, the improvement comprising wherein the crude tetrahydrofuran and water mixture without separation and before distillation is contacted in the vapor form with a dilute liquid sodium hydroxide solution at a concentration of from 5 to 35% by weight of sodium hydroxide, thereby reducing the COD of the water removed in the subsequent distillation.

2. The improvement of claim 1 wherein the dilute liquid sodium hydroxide is from 15 to 25% sodium hydroxide.

3. In the process of cyclizing 1,4-butanediol to form a mixture of crude tetrahydrofuran and water, the water having a high chemical oxygen demand the improvement comprising wherein the mixture of crude tetrahydrofuran and water is contacted in the vapor form with a dilute liquid sodium hydroxide solution at a concentration of from 5 to 35% by weight of sodium hydroxide and the vapor mixture is then contacted with a concentrated liquid sodium hydroxide solution at a concentration of from 35 to 55% by weight sodium hydroxide, allowed to separate into two layers, a sodium hydroxide layer and a tetrahydrofuran layer, the layers are separated and the sodium hydroxide layer is concentrated to remove water extracted by the concentrated sodium hydroxide solution, the water having a reduced chemical oxygen demand.

4. The improvement of claim 7 wherein the dilute sodium hydroxide is from 15 25% sodium hydroxide.

5. The improvement of claim 7 wherein the concentrated sodium hydroxide is from 40 to 50% sodium hydroxide.

6. The improvement of claim 7 wherein the dilute sodium hydroxide is from 15 to 25% and the concentrated caustic from 40 to 50% sodium hydroxide.

* * * * *

UNITED STATES PATENT OFFICE
CERTIFICATE OF CORRECTION

PATENT NO. : 4,197,248
DATED : April 8, 1980
INVENTOR(S) : Harry B. Copelin and Thomas D. Canby It is certified that error appears in the above-identified patent and that said Letters Patent are hereby corrected as shown below:

Column 8, line 41, "7" should be -- 3 --.

Column 8, line 42, between "15 25%" insert -- to --.

Column 8, lines 43 and 46, the claim reference numeral "7", each occurrance, should read -- 3 --.

Signed and Sealed this

Twelfth Day of August 1980

[SEAL]

Attest:

SIDNEY A. DIAMOND

*Attesting Officer*  *Commissioner of Patents and Trademarks*